United States Patent
Earhart et al.

(10) Patent No.: US 8,481,336 B2
(45) Date of Patent: Jul. 9, 2013

(54) MAGNETIC SEPARATION DEVICE FOR CELL SORTING AND ANALYSIS

(75) Inventors: Christopher M. Earhart, Palo Alto, CA (US); Shan X. Wang, Portola Valley, CA (US); Robert J. Wilson, Campbell, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 397 days.

(21) Appl. No.: 12/807,625

(22) Filed: Sep. 9, 2010

(65) Prior Publication Data

US 2011/0059468 A1    Mar. 10, 2011

Related U.S. Application Data

(60) Provisional application No. 61/276,303, filed on Sep. 9, 2009.

(51) Int. Cl.
*G01N 33/553* (2006.01)
*B01D 63/00* (2006.01)

(52) U.S. Cl.
USPC ....... 436/526; 435/4; 210/321.6; 210/500.27; 210/488

(58) Field of Classification Search
USPC ............... 436/526; 435/4; 210/321.6, 500.27, 210/488
See application file for complete search history.

(56) References Cited

U.S. PATENT DOCUMENTS

| | | | |
|---|---|---|---|
| 6,623,984 B1 | 9/2003 | Fleischman et al. | |
| 7,666,308 B2 | 2/2010 | Scholtens et al. | |
| 2006/0254972 A1* | 11/2006 | Tai et al. | 210/321.6 |
| 2007/0117158 A1 | 5/2007 | Coumans et al. | |
| 2007/0181466 A1* | 8/2007 | Wang et al. | 209/38 |

OTHER PUBLICATIONS

Riethdorf et al., "Detection of circulating tumor cells in peripheral blood of patients with metastatic breast cancer: A validation study of the CellSearch system", 2007, pp. 920-928, Clinical Cancer Research v13n3.

* cited by examiner

*Primary Examiner* — Mark Shibuya
*Assistant Examiner* — Pensee Do
(74) *Attorney, Agent, or Firm* — Lumen Patent Firm

(57) ABSTRACT

A magnetic sifter is adapted for manipulation of biological cells by providing a greater pore density at the edge of the sifter than at the center. Application of an external magnetic field to the sifter causes high magnetic fields and field gradients at the sifter pores. These conditions are suitable for capturing magnetically tagged or labeled cells at the sifter pores. Altering the external magnetic field can provide controlled capture and/or release of magnetically labeled cells from the sifter pores. The purpose of having a greater pore density at the periphery of the sifter than at the center is to provide improved flow rate uniformity through the sifter. Such flow rate uniformity is advantageous for cell quantification.

18 Claims, 5 Drawing Sheets

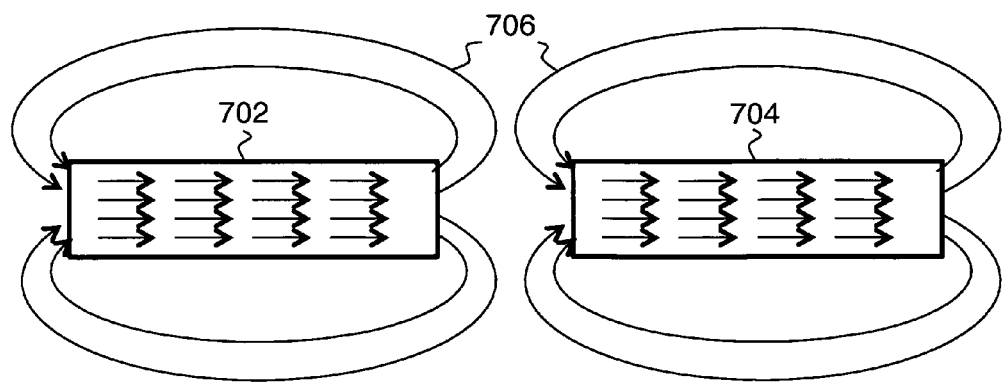
Fig. 7a
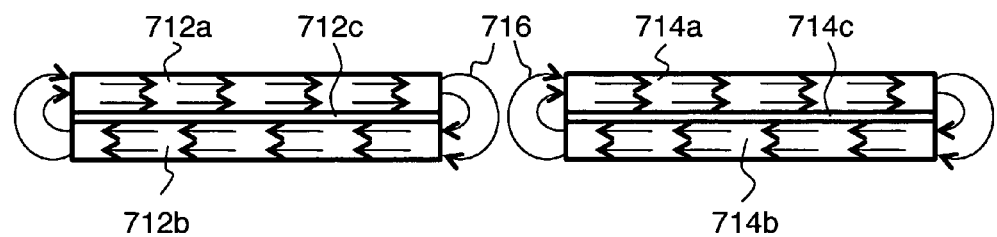
Fig. 7b
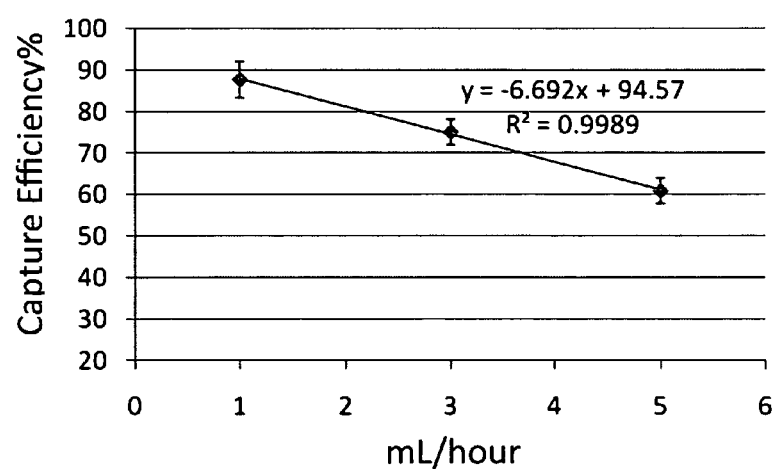

MAGNETIC SEPARATION DEVICE FOR CELL SORTING AND ANALYSIS

CROSS REFERENCE TO RELATED APPLICATIONS

This application claims the benefit of U.S. provisional patent application 61/276,303, filed on Sep. 9, 2009, entitled "Magnetic separation device for cell sorting and analysis", and hereby incorporated by reference in its entirety.

GOVERNMENT SPONSORSHIP

This invention was made with Government support under contract number NCI 1U54CA119367 awarded by the National Cancer Institute. The Government has certain rights in this invention.

FIELD OF THE INVENTION

This invention relates to magnetic methods for handling biological cells.

BACKGROUND

Numerous biomedical applications require rapid and precise quantification of biological cells and/or molecules in a sample. One approach for performing such quantification is to employ magnetic probes which can bind to the species of interest and be captured by a magnet. For example, a wall of a device can contain a magnet, and species that have magnetic probes attached can be captured at the wall. However, such approaches can suffer from several shortcomings, such as large size, low capture rate, and cumbersome release methods.

For the specific case of biomolecules, a magnetic sifter approach was considered in US 2007/0181466, hereby incorporated by reference in its entirety. The magnetic sifter has pores that pass through a substrate such that a soft magnetic material is present near the pores. With this arrangement, magnetically labeled biomolecules can be captured at and released from the pores of the sifter by using an external magnetic field to alter the magnetic field produced by the soft magnetic material at the pores.

Controllably capturing and releasing biomolecules from the pores of a magnetic sifter is substantially easier than performing the same operation for biological cells, because molecules are smaller than cells and have more predictable behavior. Accordingly, it would be an advance in the art to provide capture and release of biological cells using a magnetic sifter.

SUMMARY

A magnetic sifter is adapted for manipulation of biological cells by providing a greater pore density at the edge of the sifter than at the center. Application of an external magnetic field to the sifter causes high magnetic fields and field gradients at the sifter pores. These conditions are suitable for capturing magnetically tagged or labeled cells at the sifter pores. Altering the external magnetic field can provide controlled capture and/or release of magnetically labeled cells from the sifter pores.

The purpose of having a greater pore density at the periphery of the sifter than at the center is to provide improved flow rate uniformity through the sifter. The pore arrangement of the sifter is preferably selected such that the flow rate distribution is substantially uniform across the channel. The pore density is greater at the edge of the sifter than at the center to compensate for the effect of fluid viscosity, which ordinarily leads to a greater flow rate at the center of a channel than at the edges of a channel.

Providing enhanced flow rate uniformity through a magnetic sifter has numerous advantages, which can be better appreciated by considering some aspects of typical biomedical applications.

Isolating cells has important applications in the research, diagnosis, and treatment of many diseases, including cancer. Often the cell populations of interest are extremely rare, with clinically relevant concentrations ranging from parts per ten thousand to parts per billion. The high capture efficiency and high release efficiency of the sifter and the option for directly quantifying cell populations make the present approach ideally suited for point of care as well as laboratory cell separations.

However, most such applications rely on cell quantification, and for cell quantification it is important for the flow rate through each pore of the sifter to be substantially the same. The reason for this is that cell capture and release rates are a function of flow rate, and a non-uniform flow rate therefore leads to non-uniform capture and/or release rates at various locations on the sifter. Such non-uniformity can lead to error, if it is incorrectly assumed that these rates are uniform across the sifter, or to increased measurement complexity, if the non-uniformity is characterized and accounted for. Thus, the advantages of providing flow rate uniformity in a magnetic sifter include improved accuracy for cell quantification and/or decreased complexity of cell quantification methods/apparatus. Flow uniformity also allows titrating fractions which elute differently depending on viscous flow rate and the number of adsorbed nanoparticles per cell.

BRIEF DESCRIPTION OF THE DRAWINGS

FIGS. 7a-b show magnetic field configurations relating to magnetic sifter operation.

FIG. 8 shows a plot of measured capture efficiency vs. flow rate through a magnetic sifter.

DETAILED DESCRIPTION

Figure 1A:
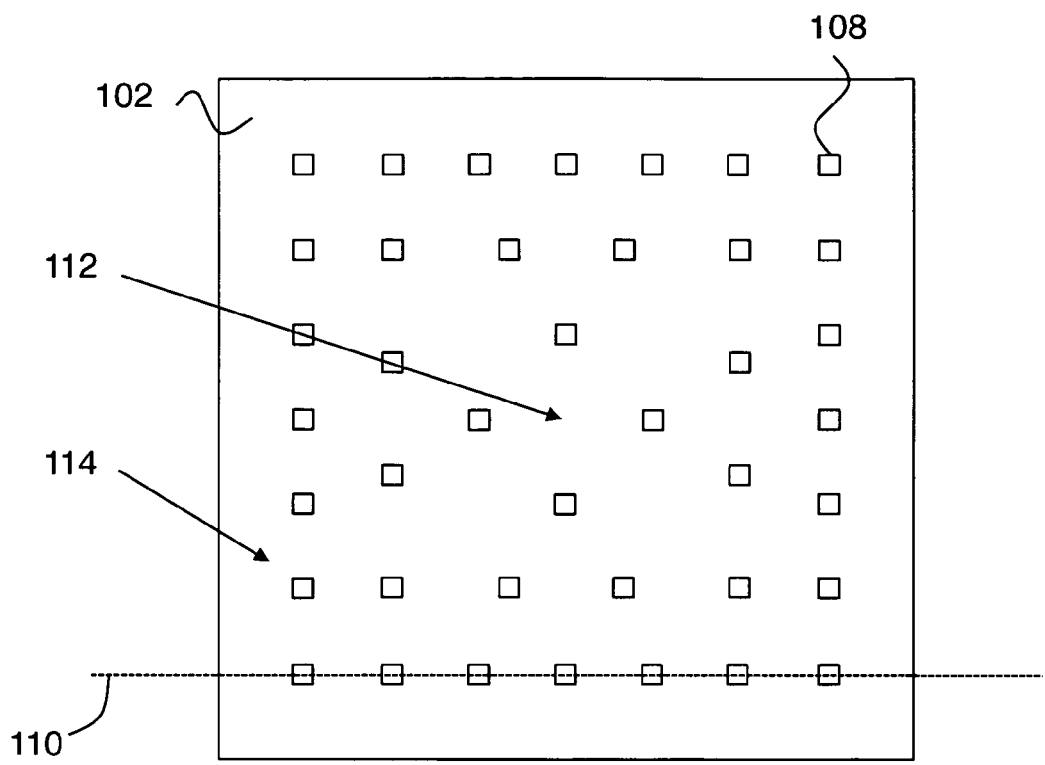
FIGS. 1a-b show top and side views of a magnetic sifter according to an embodiment of the invention.

In the present work, a magnetic sifter is adapted for manipulation of biological cells by providing a greater pore density at the edge of the sifter than at the center. The top and side views of FIGS. 1a and 1b, respectively, show an example, where a substrate 102 and soft magnetic layer 104 form a layered structure through which several pores pass, one of which is referenced as 108. The side view of FIG. 1b is taken along line 110 on FIG. 1a. The pore density at a peripheral region 114 of the sifter is greater than the pore density of a central region 112 of the sifter. The pore density can smoothly increase from center to edge (e.g., as shown on FIG. 1a), or discrete central and peripheral regions can be formed, where the pore density is constant in each region. In cases where the central and peripheral regions are discrete, any number of intermediate regions can be included between the central and peripheral regions. Optionally, anti-fouling layers can be disposed at the substrate surface 118 and/or magnet surface 120 of the magnetic sifter.

In operation, an external magnetic field 106 is provided by a magnetic source 116. Magnetic source 116 can be a permanent magnet, or it can be an electromagnet. Application of external magnetic field 106 to the sifter causes magnetization in layer 104, which tends to provide high magnetic fields and field gradients at the sifter pores. These conditions are suitable for capturing magnetically tagged or labeled cells at the sifter pores. In this description, the terms "tagged" and "labeled" are used interchangeably to refer to cells having an attached magnetic marker. As described in greater detail below, altering external magnetic field 106 can provide controlled capture and/or release of magnetically labeled cells from the sifter pores.

The purpose of having a greater pore density at the periphery of the sifter than at the center is to provide improved flow rate uniformity through the sifter. FIGS. 2a-b show an example. FIG. 2a shows a typical flow rate distribution 204 in a channel 202. The flow rate is greatest at the center of the channel and decreases towards the edges of the channel as a result of fluid viscosity. The side view of FIG. 2b shows such a channel after addition of a magnetic sifter 208 having greater pore density at the sifter periphery than at the sifter center (e.g., as shown on FIG. 1a). The pore arrangement of sifter 208 is preferably selected such that the flow rate distribution 206 is substantially uniform across the channel, as shown.

By having a greater pore density at the sifter periphery than at the sifter center, greater resistance is provided to fluid flow at the center of the channel than at the edge of the channel. This effect can be tailored to compensate for the flow rate distribution in an empty channel (e.g., as shown on FIG. 2a), thereby providing the desired flow rate uniformity. Detailed design of sifter hole patterns in accordance with these principles depends on details of channel/flow cell geometry and on the properties of the fluid being employed, especially its viscosity. Providing such detailed designs in accordance with these principles is within the skill of an art worker.

Figure 1B:
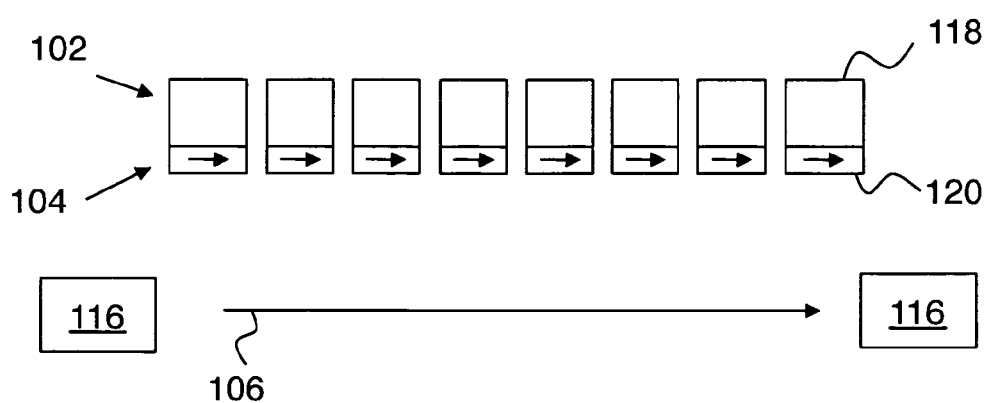
Figure 2A:
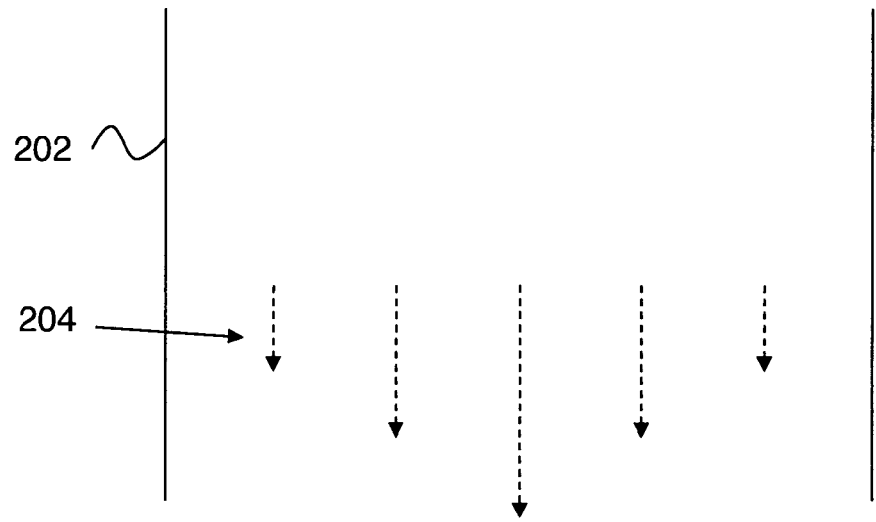
FIGS. 2a-b schematically show laminar flow in a tube and uniform flow in a tube having a magnetic sifter.
Figure 2B:
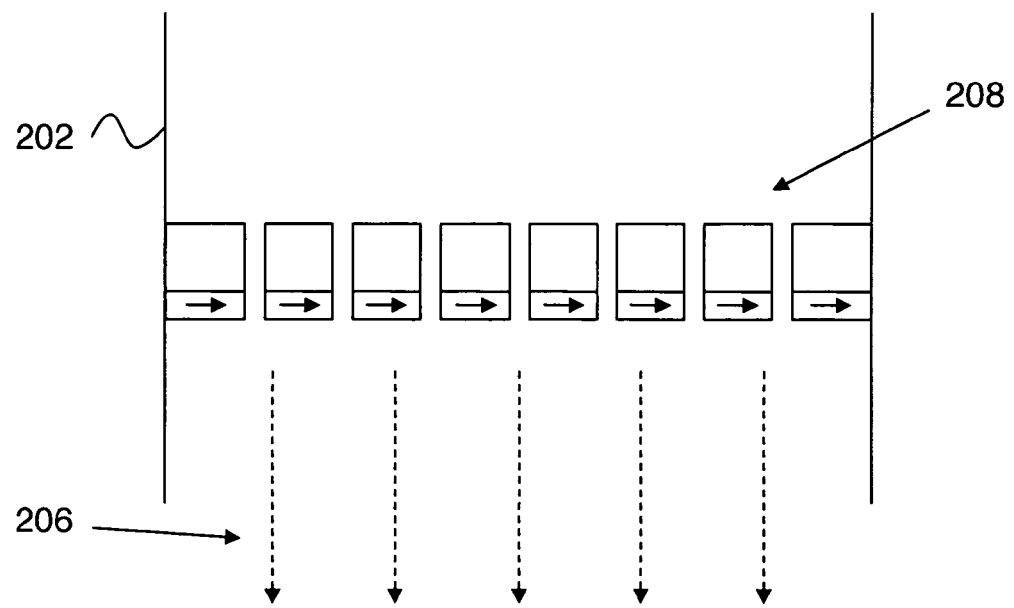
Figure 3:
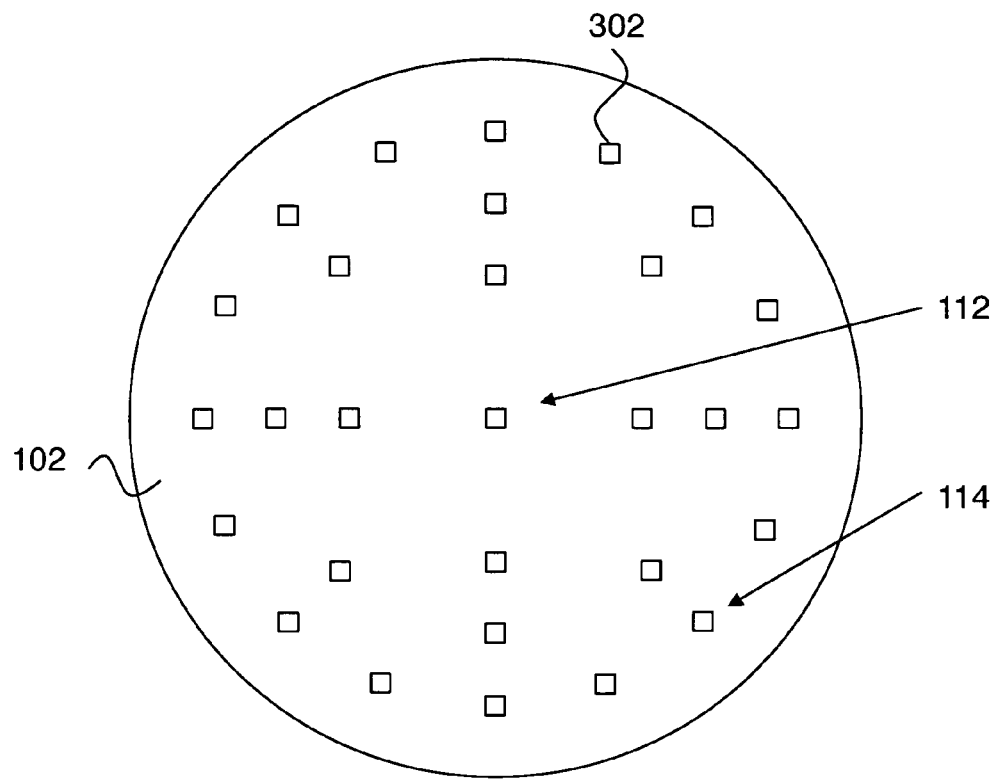
FIG. 3 shows a top view of an alternate embodiment of the invention.

Practice of the invention does not depend critically on the geometrical details of FIG. 1a. Any pore arrangement having a greater pore density at the periphery of the arrangement than at the center of the arrangement can be employed. FIG. 3 shows an example of a circular arrangement, where the pore density is a smoothly increasing function of radius. Here, one of the pores is referenced as 302.

Figure 4:
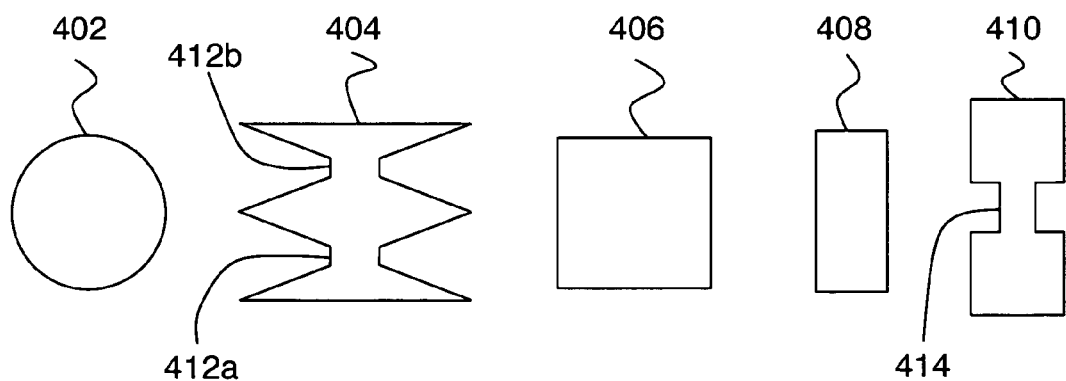
FIG. 4 shows several possible pore shapes for magnetic sifters.

Practice of the invention also does not depend critically on the shape of the sifter pores. Several possible pore shapes are shown on FIG. 4. These examples include circular pores (402), bow-tie pores (404), square pores (406), rectangular pores (408), and notched rectangle pores. (410). For the bow-tie and notched rectangle pores, there are focus points (e.g., 412a, 412b and 414) which tend to be preferential sites for cell capture. The focus points can have flat tips (as shown) or sharp tips. Pore sizes can range from less than one micrometer wide to about 100 micrometers wide. For applications in cell separation, the slit width can be chosen to be slightly larger than the average diameter of cells in a mixture, and the slits may be square in shape.

Figure 5:
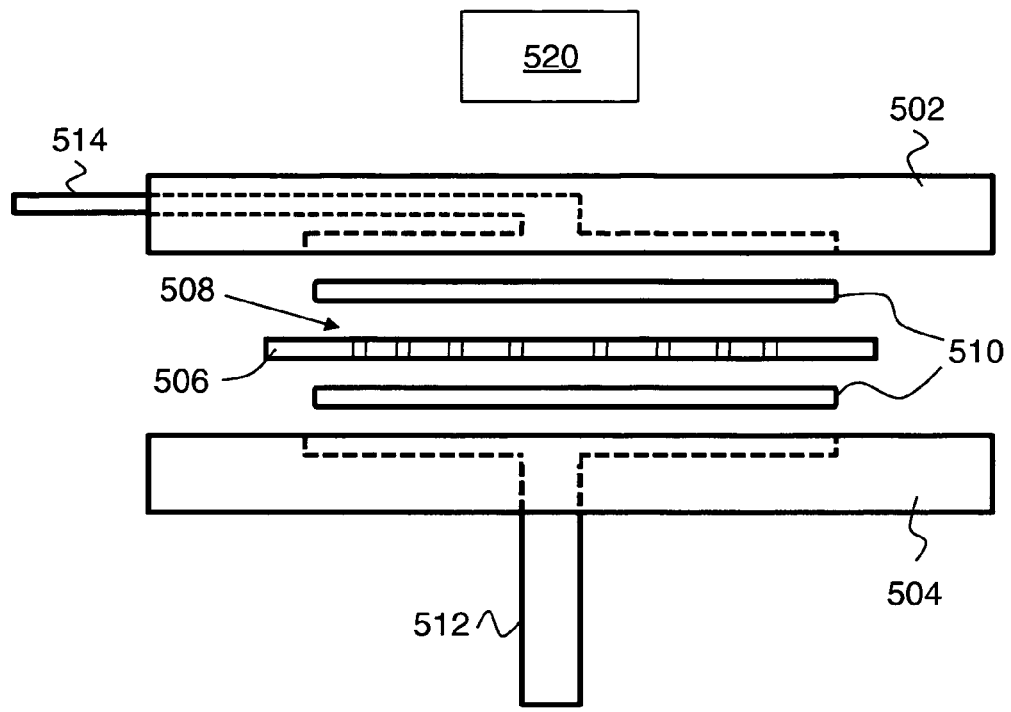
FIG. 5 shows an arrangement where a magnetic sifter is placed in a flow cell such that optical characterization of captured particles/cells can be performed.

In a preferred embodiment, a magnetic sifter as described above is included in a flow cell that includes an optical window in proximity to the pores of the sifter. FIG. 5 shows an example in exploded view. A magnetic sifter 506 including pores (i.e. through holes) 508 is clamped between O-rings 510 by flow cell members 502 and 504 which provide a fluid connection (dashed lines) between channels 512 and 514 that passes through magnetic sifter 506. An optical instrument 520 is disposed such that light from the pores of the sifter can reach instrument 520. In this example, flow cell member 502 is fabricated from a clear material (e.g., transparent plastic), and can serve as the optical window. Alternatively, a transparent window (not shown) can be included in an otherwise opaque flow cell member 502 to provide optical access to captured cells.

This embodiment can be interfaced with a fluidic system, and can be employed to capture and release cells, including circulating tumor cells, stem cells, hematopoietic progenitor cells, cardiac progenitor cells, etc. Flushing with a buffer or cell culture media solution can be employed in connection with this embodiment to harvest the captured cells for subsequent analysis or cell culturing.

Figure 6:
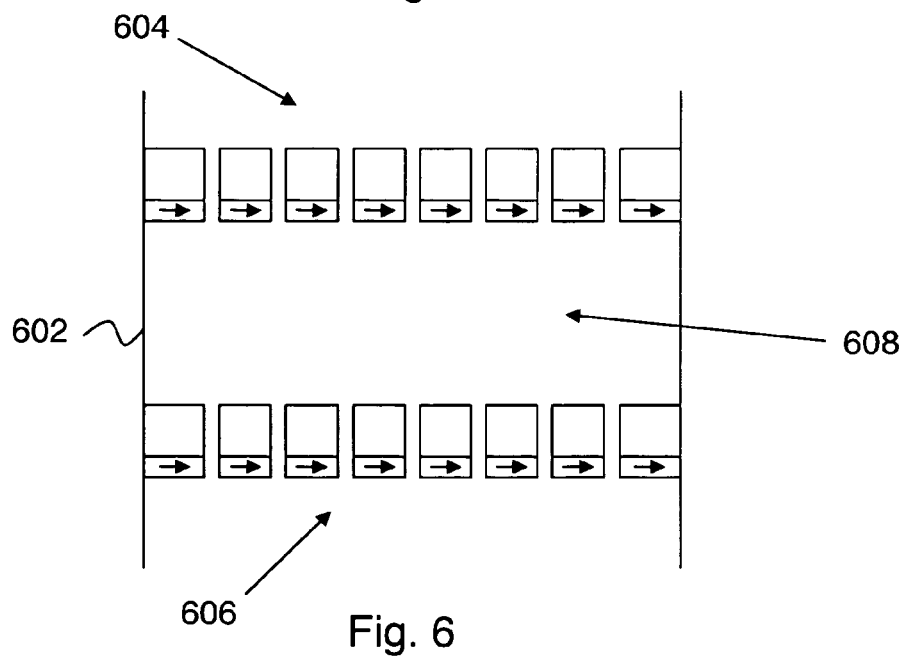
FIG. 6 shows cascaded magnetic sifters.

Embodiments of the invention are suitable for sequential processing of biological cells. FIG. 6 shows a simple example, where a channel 602 includes a first magnetic sifter 604 and a second magnetic sifter 606. The operation of first sifter can provide a processed cell stream 608 between first sifter 604 and second sifter 606. This processed cell stream can then serve as an input to the second sifter 606. Any number of sifters can be cascaded in this manner. The magnetic tags used for the several sifters in such an arrangement can be the same or they can be different.

Stacking of sifters also enables multiplex magnetic separation. For example, to perform a two-plex separation, two sifters can placed in series as shown on FIG. 6. A cell suspension can be mixed with two magnetic particles with distinctly different properties (e.g., magnetic saturation fields, saturation magnetizations, and/or particle sizes) and distinctly different targeting/capture antibodies specific to two different cell types. To illustrate two-plex separation, we consider labeling cell suspensions with two particles with different saturation fields, referred to as particle A (low saturation field) and particle B (high saturation field). For an arbitrary magnetic sifter design, particle A will be easier to capture, due to a lower saturation field, while particle B will be more difficult to capture. The two sifters can be designed such that the first sifter 604 generates on average a weaker magnetic field gradient in the pore than the second sifter 606. The average field gradient across a sifter pore can be tuned by varying the applied external field strength, pore width, sifter magnetic film thickness, and/or the saturation magnetization of the sifter film. Since the average field gradient of a pore depends linearly with the saturation magnetization of the film, sifter films with variable alloy compositions could be an elegant approach to tuning the average gradients.

In this scheme, cells labeled with particle A, the easier of the two particles to capture, are captured by the first sifter 604 with weak magnetic field gradients. Cells labeled with particle B pass through the first sifter uncaptured and are included in processed cell stream 608. The cells labeled with particle B are then subjected to the significantly higher magnetic field gradients of the second sifter 606, and are therefore captured on the second sifter. The sifter holder can allow the two sifters to be detached and washed separately, yielding two eluted solutions containing enriched cells labeled with either A particles or B particles.

In the case of cell separation, one issue is variation in surface antigen expression which could lead to variations in magnetic particle loading. For example, EpCAM expression can vary between approximately a few thousand to several hundred thousand antigens per cell across tumor types. If cells are saturated by magnetic particles, a cell labeled with 2000 of particle A will be harder to capture than a cell labeled with 500,000 of particle B. This may be addressed by functionalizing particles appropriately based on known or suspected levels of antigen expression (i.e. labeling cells with low antigen expression with high-saturation field magnetic particles), or varying the amounts of each magnetic nanoparticle type added. It may also be helpful to further tune the saturation fields of the magnetic particles as well as the applied external fields experienced by each sifter to generate maximum differences in particle moment. The difference in average magnetic field gradient can also be increased by a factor of 100 or more, by tuning both the magnetization of the sifter film, film thickness, and pore width.

This approach could enable multi-target CTC selection. In multi-target CTC separation, tumor cells are targeted for multiple antigens, such as EpCAM, cytokeratin, Her-2/neu, and/or Mucin1. One approach would be to employ the two-plex separation using magnetic particles with different magnetic saturation fields described above. Here, particles which are difficult to capture (e.g. Particle B) are coated with an antibody, such as anti-Mucin1, anti-Her-2/neu, or anti-cytokeratin, specific to an antigen that has generally low expression levels by CTCs. Particle A, which are easy to capture, are coated with an antibody, such as anti-EpCAM, which generally has high expression by CTCs. Cells with high EpCAM expression, with varying expressions of the alternative target antigen, will have large amounts of Particle A loading, and will thus be captured on the first of two sifters in series. Cells with weak or absent EpCAM expression, but expression of the alternative target antigens, and hence particle B, will be captured on the second sifter with higher average magnetic field gradients.

In order to facilitate release of captured cells, a non-magnetic spacer layer can be incorporated into the sifter. FIGS. 7a-b show an example. Here, FIG. 7a shows a close up side view of the soft magnetic layer (702 and 704) on either side of a sifter pore. FIG. 7b shows an alternate configuration, where two soft magnetic layers (712a, 714a) and (712b, 714b) on either side of a sifter pore are vertically separated by a non-magnetic spacer layer (712c, 714c). The arrangement of FIG. 7b facilitates the formation of oppositely directed magnetization in the two soft magnetic layers in a demagnetized state resulting in flux closure and reduced leakage flux at the magnetic film's edges when unmagnetized. This reduction in leakage flux can prevent stray magnetic field gradients from trapping magnetically-tagged capture probes or cells at the sifter surface when the external applied magnetic field is removed. This effect is schematically shown with field distributions 716 and 706.

Capture probe and cell release can also be expedited by the use of agitation of the sifter surface through ultrasonic vibration or other mechanical stirring. This can be accomplished by inserting the sifter into a small container containing buffer solution, and placing the container into an ultrasonic bath for 1-5 minutes. Also, mechanical stirring can be incorporated directly into the sifter device by bonding piezoelectric plates onto the top and bottom surfaces of the magnetic sifter. The piezoelectric plates can be actuated by applying an alternating current voltage. With proper amplitude and frequency of the applied signal, mechanical vibration of the plates can be transferred to the magnetic sifter substrate and membrane, resulting in release of any attached capture probes and cells.

Capture probe and cell release can also be expedited by switching the direction of the applied field while flushing the sifter with buffer solution. Switching the direction of the applied field 90 degrees changes the orientation of the fringing field across a pore, thus switching the locations of highest field gradients to the adjacent pore edges. Capture probes and magnetically tagged cells will then follow the magnetic field gradients. If fluid is flushed through the sifter at sufficiently high velocity, capture probes and cells can be flushed through the pores during the switch in applied magnetic field direction.

Capture probe and cell release can also be improved by demagnetizing the sifter using an externally applied AC field applied by an electromagnetic source, such as a solenoid magnet with an alternating current through it. Although a magnetically soft material is chosen for the sifter surface, some magnetic remanence results in non-zero magnetization at zero field. The remanent magnetization can result in field gradients capable of capturing, or holding onto, magnetically tagged capture probes and cells. The effect of this remanence can be reduced or removed by sweeping a small applied field near zero field strength during release.

As indicated above, anti-fouling layers can be employed to improve sifter performance. The sifter surface(s) can be treated with an anti-adhesion layer, such as Tridecafluoro 1,1,2,2-tetrahydrooctyl-trichlorosilane (FOTS). FOTS is a commonly employed antiadhesion layer for nanoimprint lithography stamps due to its low-energy surface. The sifter surface can also be treated with antifouling layers such as poly (ethylene glycol), phosphotidylcholine, or carboxybetaine based polymers, or Pluronic surfactants. These layers are commonly employed on the surfaces of biosensors and medical implants to prevent non-specific protein adsorption and cell attachment to the surface. To allow for chemical coupling of an antiadhesion or antifouling layer, the magnetic film on the sifter surface can by coated with a chemically convenient layer, such as a thin layer of gold or silicon dioxide, for performing surface modification. To attach a surfactant such as Pluronic, the sifter can simply be incubated in an aqueous pluronic solution prior to use.

In preferred embodiments of the invention, cell capture at a magnetic sifter is combined with quantification of the captured cells. Tagging of captured cells with fluorescent, colorimetric, radiological, plasmonic, chemiluminescent, and/or Raman tags can be employed in connection with this embodiment to provide quantitative results for captured cells. Tagged cells can be counted and distinguished based on observed color, radiation, plasmonic emission, Raman scattering, etc. Multiplex cell quantification by utilizing fluorophore-antibody conjugates with distinct emission spectra can also be performed in connection with this embodiment.

For example, one or more fluorescent markers can be employed that selectively bind to specific cell types. 3-color marking schemes can be employed. For example, a first fluorescent marker can be used that binds specifically to a first cell type, a second fluorescent marker can be used that binds specifically to a second cell type, and a third fluorescent marker that labels all cell types (e.g., nuclear stain 4',6-diamidino-2-phenylindole (DAPI)) can be used to help distinguish cells from fluorescent debris. Use of these three fluorescent markers simultaneously will provide improved specificity for quantifying the first and second cell types.

This approach is suitable for clinical evaluation using patient blood samples. For example, cancer can be clinically evaluated in this manner by magnetically sifting and quantifying circulating tumor cells in a patient blood sample. Similarly, HIV or other disease states can be clinically evaluated in this manner by magnetically sifting and quantifying lymphocytes in a patient blood sample.

EXPERIMENTS

Several experiments have been performed using magnetic sifters for capturing and releasing biological cells. The magnetic sifter configuration in these experiments is similar to the above-described magnetic sifters, except that the sifters used in these experiments did not have a higher pore concentration at the sifter edge than at the sifter center. Instead, the pore density was the same at the center and the edge of the sifter. Despite this difference, the encouraging results of the following experiments are expected to also apply to sifters having higher pore concentration at the edge than at the center. These experiments generally relate to analysis of blood samples, where it is important to distinguish abnormal cells (e.g., circulating tumor cells (CTCs)) from normal cells such as red blood cells (RBCs) and white blood cells (WBCs).

Experiment 1

H1650 Separations from Whole Blood, Pretagged

There are several key advantages to working with whole blood, as opposed to a lysed blood sample with the RBCs removed. First, the time between blood sample acquisition and processing with the sifter is reduced. Although lysing the blood is fairly straightforward, the 15 minutes of incubation with the lysis buffer and 2 washing steps requiring 10 minutes of centrifuging each, typically results in an additional hour of sample preparation prior to the capture step. Second, RBC lysis can result in nucleated cell loss (i.e. non-RBCs), either due to non-specific lysis or loss due to sample handing during the washing steps. Third, the activation of WBC cells may be reduced if the WBC are left in their native environment prior to processing with the sifter, leading to less adhesion to the sifter surface and higher and more accurate purity measurements.

Differences in WBC adhesion between lysed and whole blood samples were observed by passing whole blood through a sifter and imaging the sifter before and after washing steps. Following passage of 200 µL of whole blood, the sifter surface appeared clean in reflectance mode. When imaging with transmitted light, the pores appeared filled with a residual solution of RBCs, as indicated by the red color of pores. Following a rinsing step of flowing 200 µL of phosphate buffered saline (PBS) through the sifter at 2 ml/hr, the sifter appeared clean in both reflectance and transmittance mode. This differs significantly from the case of passing lysed blood through the sifter, where the sifter surface is decorated with remaining white blood cells even after repeated washing with pluronic solution and PBS buffer.

In addition to working with whole blood, a method for spiking low, clinically relevant concentrations of H1650 into blood samples was developed. Here, H1650 refers to a non-small-cell lung cancer (NSCLC) cells (NCI-H1650). Previous experiments relied on serial dilutions and verification of concentration with the hemocytometer to prepare H1650 samples with known concentrations. The hemocytometer is only accurate for cell concentrations greater than a few thousand cells per ml, since the volume counted with the hemocytometer is contained within a square region 9 mm$^2$ in area and a height of 100 µm. For a sample with an actual concentration of 1000 cells/ml, only one cell is expected to be found in this entire volume ($9 \times 10^{-4}$ ml). To prepare low concentration samples, a method was developed in which a small (~5 µL) droplet of H1650 cells was pipetted onto the inside of a centrifuge cap. The H1650 were then allowed to settle to the surface, which took approximately 30 seconds for magnetically labeled cells using a magnetic field to accelerate sedimentation, and a few minutes for non-magnetically labeled cells by gravity. The droplet was then imaged with fluorescence microscopy, and the exact number of H1650 cells was counted. Samples ranging from 1-200 cells are readily prepared. Beyond that, counting becomes tedious without the aid of counting grids on the inside of the centrifuge tube. Whole, untreated blood was then added to the centrifuge tube, the cap was closed, and the H1650 and blood sample were mixed by gentle inversion.

In these experiments, H1650 were fluorescently and magnetically labeled prior to spiking into whole blood. Quantification of the H1650 was performed by counting captured cells on the sifter surface, since the background concentration of RBCS prohibited the use of the hemocytometer or flow cytometry. In these experiments, 0.5 mL of whole, untreated blood samples containing ~100±20 H1650 cells/ml were processed with sifters containing 40 µm pores. In this work, it was important to ensure that magnetic field gradients at locations other than the sifter pores were sufficiently small to prevent capture at locations other than the sifter pores.

Separations were performed on 0.5 mL whole blood samples containing pre-fluorescently and pre-magnetically labeled H1650 at concentrations of 50-100 H1650/mL. Following separation, the sifters were removed from the flow apparatus and imaged by fluorescent microscopy, and the number of H1650 cells on the sifter surface was compared with the known number of H1650 spiked into the blood sample. H1650 were then eluted by reinserting the sifter into the flow apparatus and flushing with 500 µL of PBS buffer in the absence of an applied magnetic field. The sifter was again reimaged to confirm the detachment of captured H1650.

H1650 cells labeled with Green CellTracker™ dye were clearly observed in the sifter pores. The cells were counted manually, requiring approximately one minute to scan over the entire sifter surface.

Capture efficiency as a function of sample flow rate was measured by varying the inlet flow velocity during the capture step from 1-5 ml/hr, and the results are shown in FIG. 8. There is a clearly linear relationship between the flow velocity and the capture yield of the separation process. The capture efficiency decreases with increasing flow rate, due to the increased linear velocity of the cells through the pores, resulting in a larger drag force. Capture yield did not increase significantly at flow rates slower than 1 ml/hr, and in fact resulted in a wider distribution of capture efficiencies. This is attributed to the increased time required to carry out the separation. At 0.5 ml/hr, the sample requires approximately 1 hour to pass through the sifter, during which the cells in the inlet tube undergo significant sedimentation to the bottom of the tube before flowing through the sifter.

The capture yields for these experiments, and the linear relationship between capture yield and flow rate were extremely encouraging, especially given the small patterned area of the sifter (~20 mm$^2$), which is on the order of 50 times smaller than most microdevices devices geared towards capturing CTCs from whole blood.

In addition to 40 µm sifters, separations were performed on H1650 spiked into whole blood using 50 µm square pores, the bowtie shaped pores discussed above, as well as 20 µm circular and square pores. Capture experiments using 50 µm pores showed no observable change in capture efficiency. Separation with the bowtie structure resulted in lower capture efficiencies (50% at 5 ml/hr), but cells were captured at predictable locations between the pole tips. This capture behavior can be advantageous when the imaging and enumeration of cells is performed automatically by an optical scanning system.

In the case of 20 μm pore sizes, it was found that the H1650 were captured from whole blood with efficiencies of 80% regardless of flow rate. After it was observed that the H1650 were captured with the same efficiency in the absence of an applied external field, and also without magnetic labeling, it became apparent that the H1650 were captured based on their comparably larger sizes and reduced deformability for the 20 μm pore sizes.

Experiment 2

Fluorescent Staining of Bare H1650 Cells

The second significant hurdle to overcome is to fluorescently label the tumor cells in a background of whole blood, in a selective manner for identification and enumeration. Experiments were thus performed on bare H1650 spiked into whole blood, without any pre-fluorescent or pre-magnetic labeling, to mimic the conditions of separating and enumerating CTCs from a clinical sample.

Differentiating a captured tumor cell from a WBC requires multi-color imaging of at least two fluorophores, one to indicate a positive expression of a surface antigen or intracellular protein specific to the tumor cell, and another to indicate positive expression of a surface antigen specific to a WBC. In preliminary experiments, captured cells were stained with biotin-PE (red) and anti-CD45-FITC (green). Tumor cells should fluoresce in the red, since they are positive for EpCAM, and hence should display the streptavidin-coated ferrofluid which is stained red by the biotin-PE. Also, a tumor cell should be absent in measurements of green fluorescence, or, negative for CD45. Likewise, WBCs should appear green, since they are positive for CD45 and are stained with anti-CD45-FTIC, while they should be absent in measurements of red fluorescence (negative for EpCAM).

Preliminary experiments staining captured H1650 with anti-EpCAM-PE revealed weak fluorescence, likely due to the saturation of EpCAM binding sites by the anti-EpCAM-biotin selection antibody. As a result, the biotin-PE was used to amplify the red fluorescence above background. In actual clinical samples, cell permeation and staining with cytokeratin, an intracellular protein specific to CTCs, will likely be used.

Human EpCAM+ Cancer Cells PlusCellect™ labeling kits and the corresponding MagCellect™ Ferrofluid were purchased from R&D Systems, Inc. The PlusCellect™ labeling kit includes a cocktail of biotinylated anti-EpCAM antibodies (concentration proprietary), a "PlusCellect™" buffer solution of proprietary composition for labeling the cells, and streptavidin-functionalized magnetic nanoparticles (MNP). The magnetic properties and manufacturer specifications of the ferrofluid are as follows: average diameter 145 nm, composition $Fe_3O_4$ (80% w/w)/Polymer Matrix, saturation field ~2000 Oe, magnetization 313 emu/cc, concentration $4\times10^{11}$ particles/mg iron (~$10^{11}$ particles/ml), and binding capacity ~15,000 small biotinylated molecules/particle (~5,000 large biotinylated molecules/particle).

In this work, the following magnetic labeling protocol was employed (Magnetic Labeling Protocol 1). H1650 pre-fluorescently labeled with Green CellTracker™ dye were added to 0.5 mL of whole blood at concentrations of approximately 100 H1650 cells/ml. 20 μL of the selection antibody was added, in addition to 100 μL of 10% Pluronic-F-68 surfactant. The sample volume was then increased to 1 mL by the addition of PlusCellect™ buffer and incubated for 15 minutes at 4° C. The sample volume was then brought to 15 mL with PlusCellect™ buffer, centrifuged at 300 G for 10 minutes, and the supernatant was removed. 40 μL of MagCellect™ Ferrofluid was added to the cell pellet, in addition to 100 μL of 10% Pluronic-F-68 surfactant. The volume was then brought to 1 mL by the addition of PlusCellect™ buffer and incubated for 20 minutes at 4° C. The sample was then washed by the addition of PlusCellect™ buffer and centrifugation, and the resulting cell pellet was then resuspended in 1 mL of PlusCellect™ buffer. The cell suspension was then processed with the sifter containing 40 μm square pores at 5 ml/hr, yielding an average capture efficiency of 53.5±4.9% over five separations.

To demonstrate feasibility, bare H1650 cells were spiked into whole blood and labeled according to Magnetic Labeling Protocol 1, described above. Following magnetic labeling, 10 μL of the biotin-PE fluorophore (mg/ml) and 20 μL of anti-CD45-FITC were added to the sample, which was then incubated for 30 minutes before washing. The blood sample was then processed with the sifter at 5 ml/hr.

Merged images of the sifter surface were inspected. In these images, the white light, red fluorescence, and green fluorescence images are merged. Red fluorescent H1650 cells are observed in the sifter pores. The H1650 cells appear on the top or bottom side of the pore, at the edge perpendicular to the direction of the externally applied field. Also observed at the edges of the pores and in regions connecting pores are deposits of unbound ferrofluid, which is also stained red during the biotin-PE labeling step. WBCs are not found anywhere on the surface, indicating they pass through the sifter uncaptured or are removed during the washing step.

To enumerate CTCs from an actual patient sample, in which CTCs may not be as uniform in size, shape, and antigen expression as a well-defined cultured cell-line, more sophisticated fluorescent labeling and imaging can be used. A typical protocol involves staining the nuclei of both CTCs and WBCs, in addition to one positive antigen of CTCs and one positive antigen of WBCs. To evaluate 3-color imaging on the sifter surface, two combinations of dyes were tested on bare H1650 cells: 1) anti-EpCAM-PE, anti-CD45-FITC, and 4',6-diamidino-2-phenylindole (DAPI), and 2) anti-cytokeratin-PE, anti-CD45-FTIC, and DAPI. Cytokeratins (CKs) are proteins found in the cytoskeletons of epithelial cells. There are both basic (CK1-9) and acidic (CK10-20) types of cytokeratin, and they are generally found in pairs. CK expression can vary across different organs or tissues, so generally a CK staining kit contains a mixture of anti-CKs specific to a few CK types. In these experiments, a mixture of anti-CK-14, 15, 16, and 19 was used. CK-19 is expressed by many carcinomas. Which varieties of anti-CK used, however, will eventually need to be optimized to result in efficient staining of CTCs regardless of origin. Anti-CK dyes require membrane permeabilization, which can be accomplished by incubating the cells in a detergent, such as 0.2% Triton surfactant. This results in a loss of cell viability. Thus, anti-EpCAM-PE was evaluated as a potential surface stain for CTCs.

DAPI is a nuclear stain that binds strongly to DNA. DAPI can pass through an intact membrane of a living cell, but passes more efficiently after cell fixation. When bound to DNA, the fluorescence of DAPI is increased about 20-fold, with excitation/emission maxima at 358/461 nm.

Merged images of an H1650 cell and a WBC on a glass slide stained with anti-EpCAM-PE, anti-CD45-FITC, and DAPI were inspected. As expected, the H1650 cell fluoresces red and blue, while the WBC fluoresces green and blue. RBCs exhibit weak background fluorescence, as they do not express EpCAM or CD45, nor possess nuclei.

To evaluate the 3-color staining of tumor cells, bare H1650 were spiked into 0.5 mL of whole blood at a concentration of ~1000 H1650/mL. Magnetic labeling was performed using Protocol 1 discussed above, and cell suspensions were separated at 5 ml/hr using a 50 µm square pore sifter. Following separation and washing with 0.5 mL PBS buffer, staining was achieved by first flowing through the sifter a 0.5 mL solution of 0.2% Triton x-100 surfactant in PBS at 5 ml/hr to permeabilize the cell membranes. 0.5 mL of PBS buffer containing 50 µL of anti-CD45-FITC stock was then flowed through the sifter at 3 ml/hr, followed by a wash with 0.5 mL PBS buffer at 5 ml/hr. 0.5 mL of PBS buffer containing 50 µL of anti-EpCAM-PE or anti-CK-PE stock was flowed through the sifter, followed by a wash with PBS. 0.5 mL of PBS containing 10 µg/mL DAPI was flowed through the sifter, followed by wash with PBS. Sifters were then removed from their holders and placed under the optical microscope for fluorescent imaging.

It was found in order to visualize the cells on the sifter surface, a high magnification objective (50×) was needed. Previous enumeration experiments with H1650 labeled with Green CellTracker™ dyes utilized a 10× objective, which allowed rapid, manual scanning over the sifter surface. For weaker surface antibody conjugated dyes, a higher magnification lens with a higher numerical aperture resulted in brighter images of cells. Only one pore array can be viewed at one time, and exposure times of 1-5 seconds are required to attain adequate brightness.

In a pore array following capture of bare H1650 spiked in whole blood, magnetically labeled with Protocol 1, and fluorescently labeled as mentioned above, fluorescence from DAPI is sufficiently strong to view through the microscope eye-piece. Fluorescence from FITC and PE require 1 second exposure times with the CCD camera. Upon merging images for DAPI, anti-CD45-FITC, and anti-EpCAM-PE fluorescence, tumor cells which are positive for nuclei and positive for EpCAM are observed captured on the sides of the pore perpendicular to the applied field direction.

The experiment was repeated using anti-CK-PE instead of anti-EpCAM-PE. H1650 cells are observed to be magnetically captured along the pore edges perpendicular to the field direction. The cells are bright blue, due to the nuclear staining of DAPI, and are negative for CD45. The fluorescence intensity of anti-CK-PE, however, is faint. This is possibly due to low expression or the absence of the specific CKs targeted by the antibodies in the anti-CK-PE kit.

Experiment 3

Clinical Sample

The labeling discussed in the previous section was repeated on a clinical sample obtained from the Stanford Cancer Center. The blood sample (~10 mL) was drawn into an evacuated Cell Free DNA blood collection tubes with a proprietary cell fixative, from a cancer patient with Stage IV lung adenocarcinoma with widespread metastases in the brain and bone. 0.5 mL of the blood sample was processed in each experiment, using Magnetic Labeling Protocol 1, and the fluorescent staining sequence described above. In each case, captured cells were stained with DAPI and anti-CD45-FITC. Both anti-EpCAM-PE and anti-CK-PE were evaluated.

Merged images of tumor cells captured from the patient sample on the sifter surface and labeled with DAPI, anti-CD45-FITC, and anti-EpCAM-PE were inspected. The captured cells are bright blue due to the nuclear staining of DAPI and are located on the edges of the pore perpendicular to the applied field direction. Both anti-CD-45-FITC and anti-EpCAM-PE fluorescence is weak, indicating that white blood cells are not captured on the sifter surface, and that EpCAM expression is low compared to H1650 cells, or the fixation process interferes with anti-EpCAM binding to the cell surface.

When cells are stained with anti-CK-PE instead of anti-EpCAM-PE, merged fluorescent images reveal captured tumor cells that are positive for both nuclei and CK. The tumor cells are once again found on the edges of the pores perpendicular to the applied field direction. Since only one array could be imaged at a time and each merged image requires 3 image acquisitions of 1 second of exposure time with manual changing of the filter set in between each acquisition, only 30 pore arrays were imaged. 82 CTCs were counted. Since there are 544 pore arrays with four 50 µm pores each, assuming that the CTCs are evenly distributed throughout the pores, this yields a CTC count of 3000 CTCs/mL of blood. A microscope with automated paneling functions capable of rapidly imaging the sifter surface can expedite CTC enumeration from patient samples. Furthermore, in all experiments the background fluorescence is appreciable, especially for red fluorescence. The background fluorescence intensity is highest on the sifter surface, and lowest inside the pores where tumor cells are usually captured. This is attributed to the reflectance configuration of the microscope, in which excitation and image collection is done from the top. The background fluorescence, which makes tumor cells appear less bright, may be reduced significantly by an alternative microscope configuration in which the cells are excited by bottom illumination and imaged on top. This would result in cells captured only within the pores from being excited and imaged by the camera.

The invention claimed is:

1. An apparatus for manipulating biological cells, the apparatus comprising:
   a substrate including a plurality of through holes and having a central region and a peripheral region around the central region, wherein the through holes have a higher density in the peripheral region than in the central region;
   one or more soft magnetic layers disposed on the substrate and in proximity to the through holes; and
   a magnetic source, wherein the magnetic source is capable of controlling a magnetic field strength and/or a magnetic field gradient provided by the soft magnetic layers.

2. The apparatus of claim 1, wherein a distribution of the through holes is selected such that flow rates through the holes are substantially the same when fluid passes through the substrate via the holes.

3. The apparatus of claim 1, wherein the shapes of the through holes are selected from the group consisting of: square holes, rectangular holes, circular holes, and bow-tie holes.

4. The apparatus of claim 1, further comprising a non-magnetic spacer layer disposed to reduce magnetic leakage flux at the soft magnetic layers when the soft magnetic layers are in a demagnetized state.

5. The apparatus of claim 1, further comprising an antifouling layer disposed at the through holes and substrate.

6. The apparatus of claim 1, further comprising a flow cell in which the substrate is disposed, wherein the flow cell includes an optical window in proximity to the through holes.

7. The apparatus of claim 1, wherein the magnetic source comprises an electromagnetic source or a permanent magnet.

8. A method for manipulating biological cells, the method comprising:
- providing a substrate including a plurality of through holes and having a central region and a peripheral region around the central region, wherein the through holes have a higher density in the peripheral region than in the central region;
- providing one or more soft magnetic layers disposed on the substrate and in proximity to the through holes;
- tagging biological cells with one or more magnetic tags to provide tagged cells;
- passing a fluid including the tagged cells through the holes of the substrate; and
- capturing and/or releasing the tagged cells at the through holes by applying an external magnetic field to control a magnetic field strength and/or a magnetic field gradient provided by the soft magnetic layers.

9. The method of claim 8, wherein a distribution of the through holes is selected such that flow rates through the holes are substantially the same.

10. The method of claim 8, wherein the releasing tagged cells comprises one or more methods selected from the group consisting of: altering the magnetic field direction at the magnets by about 90 degrees; setting the external magnetic field to about zero; reducing the external magnetic field to about zero in a manner that provides demagnetization of the magnets, and mechanically agitating the substrate and/or fluid passing through the holes.

11. The method of claim 8, further comprising quantifying cells that are captured at the through holes.

12. The method of claim 11, wherein the quantifying cells includes providing one or more fluorescent markers that bind to specific cell types.

13. A method for manipulating biological cells, the method comprising:
- first performing the method of claim 8 to provide a processed cell stream;
- second performing the method of claim 8 one or more additional times on the processed cell stream.

14. The method of claim 13, wherein the magnetic tags for the first performing differ from the magnetic tags for the second performing.

15. A method for clinical evaluation comprising:
- capturing cells from a patient blood sample according to the method of claim 8 to provide captured cells; and
- quantifying the captured cells.

16. The method of claim 15, wherein the quantifying the captured cells includes providing a first fluorescent marker that binds specifically to a first cell type, a second fluorescent marker that binds specifically to a second cell type, and a third fluorescent marker that binds specifically to both the first cell type and the second cell type.

17. A method for clinical evaluation of cancer comprising clinically evaluating circulating tumor cells according to the method of claim 15.

18. A method for clinical evaluation of disease states comprising clinically evaluating lymphocytes according to the method of claim 15.

* * * * *